(12) United States Patent
Leipprand et al.

(10) Patent No.: US 6,437,190 B1
(45) Date of Patent: Aug. 20, 2002

(54) PREPARATION OF ALDOLS USING A MICROSTRUCTURED REACTION SYSTEM

(75) Inventors: Inga Leipprand, Flörsheim; Thorsten Lahrs, Bad Vilbel, both of (DE)

(73) Assignee: Siemens Axiva GmbH & Co. KG (DE)

( * ) Notice: Subject to any disclaimer, the term of this patent is extended or adjusted under 35 U.S.C. 154(b) by 0 days.

(21) Appl. No.: 10/002,266

(22) Filed: Nov. 2, 2001

(30) Foreign Application Priority Data

Nov. 7, 2000 (DE) ......................................... 100 55 758

(51) Int. Cl.[7] .............................................. C07C 45/00
(52) U.S. Cl. ....................... 568/312; 568/313; 568/343; 568/345; 568/388; 568/390; 568/420; 568/433; 568/461
(58) Field of Search ................................ 568/312, 313, 568/343, 345, 388, 390, 433, 461, 420

(56) References Cited

U.S. PATENT DOCUMENTS

| 4,165,339 A | | 8/1979 | Reichle ....................... 260/586 |
| 4,476,324 A | * | 10/1984 | Reichle ....................... 568/388 |
| 4,701,562 A | * | 10/1987 | Olson ......................... 568/390 |
| 4,704,478 A | * | 11/1987 | Olson ......................... 568/388 |
| 5,904,424 A | | 5/1999 | Schwesinger et al. ...... 366/336 |
| 6,255,541 B1 | | 7/2001 | Paatero et al. .............. 568/862 |
| 6,299,657 B1 | | 10/2001 | Schubert et al. ............. 48/197 |

FOREIGN PATENT DOCUMENTS

| WO | WO 95/30476 | * | 11/1995 |
| WO | WO 00/51720 | * | 9/2000 |

OTHER PUBLICATIONS

Nondek, "A Tubular Micro–Reactor For Measurement Of The Kinetics Of Liquid Phase Heterogeneous Reactions Under Pressure", *J. Res. Inst. Catalysis*, Hokkaido Univ., vol. 27 No. 1, pp. 7–16 (1979).*

Moggie *et al.*, "Gas phase aldol condensation of n–butyraldehyde to 2–ethylhexenal", *Applied Catalysis*, 68, pp. 285–300 (1991).*

Abstract of JP 09–057108 (1997).
Abstract of WO 98/29374 (1998).

* cited by examiner

*Primary Examiner*—Michael L. Shippen
(74) *Attorney, Agent, or Firm*—Connolly Bove Lodge & Hutz LLP

(57) ABSTRACT

A process for preparing aldols by catalytic reaction of aldehydes and/or ketones comprises conducting said reaction in the channels of a microstructured reaction system.

14 Claims, No Drawings

PREPARATION OF ALDOLS USING A MICROSTRUCTURED REACTION SYSTEM

DESCRIPTION

This invention relates to a process for preparing aldols by catalytic reaction of aldehydes and/or ketones.

The preparation of aldols by reacting aldehydes with themselves or with other aldehydes, reacting aldehydes with ketones or reacting ketones with themselves or with other ketones using a basic catalyst is a standard reaction of organic synthesis. These reactions are therefore also referred to in general as aldol reactions (cf. ORGANIKUM, 18th EDITION, DVW, BERLIN 1990). The chemical industry also utilizes the aldol reaction, for example for preparing acetaldol from acetaldehyde (cf. ULLMANN'S ENCYCLOPEDIA OF INDUSTRIAL CHEMISTRY, SIXTH EDITION, 1999 ELECTRONIC RELEASE). The aldol reaction can be followed by a dehydration of the aldol to form an unsaturated aldehyde or ketone.

Prior art processes comprise various restrictions with regard to the conduct of the reaction. First, the maximum reaction temperature can be limited by the lowest boiling temperature of one of the components when an atmospheric operation is practiced. This limits the reaction rate and hence also the space-time yield; longer residence times can reduce the selectivity. There are also restrictions due to the heat removal performance of the apparatus used and due to safety engineering aspects of the exothermic reaction. These include for example a slow rate of metering or the use of a small quantity of catalyst. In these cases too the reaction rate and hence also the space-time yield is restricted and the selectivity impaired.

It is an object of the present invention to provide an aldol production process providing an improved space-time yield, conversion or selectivity or less costly alternatives.

This object is achieved according to the invention when, in a process of the type mentioned at the outset, the reaction is conducted in the channels of a microstructured reaction system.

The present invention accordingly provides a process for preparing aldols by catalytic reaction of aldehydes and/or ketones, which comprises conducting said reaction in the channels of a microstructured reaction system.

Microstructured systems for the purposes of the invention are microcomponents, especially reaction systems, which have been manufactured at least partly by microtechnology and precision apparatus building. The characteristic dimensions of the internal structures of the microcomponents, such as channels, are typically in the submicrometer to submillimeter range (cf. ULLMANN'S ENCYCLOPEDIA OF INDUSTRIAL CHEMISTRY, SIXTH EDITION, 1999 ELECTRONIC RELEASE). Microstructured components can be used for rapidly mixing the reactants and/or for exactly setting the desired temperature. The temperature control possibility relates to the heating of the reactants, the maintenance of a constant reaction temperature and cooling of the reaction solution to end the reaction.

Useful microcomponents include especially micromixers as described in DE 197 46 583 A1 and U.S. Pat. Nos. 5,904,424 or micro heat exchangers which are also useful as reactors (e.g. as described in DE 195 41 266 A1). These components are also useful for rapidly heating the mixture of raw materials.

Particular embodiments where a heterogeneous catalyst has been introduced into said microstructured reaction system. The catalyst is preferably selected from the group consisting of basic anion exchangers, metal oxides of Mo, W, Ca, Mg and Al and basic zeolites. The aldehyde $R_1CHO$ is reacted with itself of with a second aldehyde $R_2CHO$ or with a ketone $R_1R_2CO$ or a ketone $R_1R_2CO$ is reacted with itself or another ketone $R_3R_4$ CO and $R_1$ to $R_4$, which are each identical or different, independently can have the following meanings:

R1 is $C_{1-12}$-alkyl, C3–C12-cycloalkyl, aryl, aralkyl having 14 or less carbon atoms, each substituted or unsubstituted;

$R_2$ is H, C1–12-alkyl, C3–C12-cycloalkyl, aryl, aralkyl having 14 or less carbon atoms, each substituted or unsubstituted;

$R_3$ is C1–12-alkyl, C3–C12-cycloalkyl, aryl, aralkyl having 14 or less carbon atoms, each substituted or unsubstituted $R_4$ is C1–12-alkyl, C3–C12-cycloalkyl, aryl, aralkyl having 14 or less carbon atoms, each substituted or unsubstituted.

The process further can comprises the use of microreactor or micromixer. A heterogeneous catalyst can be introduced into the micromixer or the microreactor.

In one embodiment of the process according to the invention, a heterogeneous catalyst may have been introduced into the microstructured system, for example by vapor deposition on the walls or by chemical or physical deposition, including especially or alternatively electrochemical deposition. The catalysts used have been described in the literature and patents, especially basic anion exchangers, metal oxides of Mo, W, Ca, Mg and Al, basic zeolites (Process and catalysts for the preparation of polyhydric alcohols by the aldol condensation of aldehydes followed by hydrogenation, E. Paatero, E. Nummi; L. Lindfors; H. Nousiainen; J. Hietala; L. Lahtinen; R. Haakana; (Neste Oy, Finland), WO 97-F1835, 19971230; Method for producing alkenal by crossed aldol condensation of saturated aldehydes using zeolite-supported base catalyst; M. Ichikawa; R. Oonishi; M. Fukui; H. Harada (Chisso Corp, Japan), JP 95-218842, 19950828; Catalyst for carrying out the aldol condensation; Reichle, Walter Thomas (Union Carbide Corp., USA)US-76-657568, 19760212).

The advantages of the process according to the invention are that the microcomponents, which contain a multiplicity of microstructured channels, make it possible for the reaction to be carried out under improved reaction conditions. The characteristic dimensions of the microchannels, i.e., the flow cross section, is in the range from 50 $\mu m^2$ to 100 $mm^2$, preferably in the range from 5000 $\mu m^2$ to 5 $mm^2$. This improvement in the reaction conditions which is brought about by the invention makes it possible to improve the space-time yield, the conversion or the selectivity of the reaction.

The reaction is conducted in the liquid phase in a continuous operation. An aldehyde $R_1CHO$ ($R_1$=C1–C12-alkyl, C5–C12-cycloalkyl, aryl, C≦14 aralkyl) is reacted with itself or with a second aldehyde $R_2CHO$ ($R_2$=H, C1–C12 alkyl, C5–C12-cycloalkyl, aryl, C≦14 aralkyl) or with a ketone $R_1$ $R_2$ CO ($R_1$, $R_2$=C1–C12-alkyl, C5–C12-cycloalkyl, aryl, C≦14 aralkyl) or a ketone $R_1R_2CO$ ($R_1$, $R_2$=C1–C12-alkyl, C5–C12-cycloalkyl, aryl, C≦14 aralkyl) is reacted with itself or another ketone $R_3$ $R_4CO$ ($R_3$, $R_4$=C1–C12-alkyl, C5–C12 -cycloalkyl, aryl, C≦14 aralkyl). All the aldehydes and ketones mentioned can each be independently unsubstituted or substituted by identical or different substituents.

The liquid phase can be retained at higher temperatures by conducting the reaction under superatmospheric pressure (from 1 to 50 bar absolute or else higher). The microstructuring permits very exact setting of the desired temperature. Even the large amounts of heat released by exothermic reactions can be safely removed. The reaction can be carried out at temperatures in the range from –10 to 250° C., preferably in the range from 50 to 200° C. The residence times of the aldehydes or ketones or aldols in the channels of the microstructured system is in the range from 0.001 to 1000 s, preferably in the range from 0.01 to 100 s. The reaction time can be extended by supplementing the microstructured system with a delay time zone which is not microstructured.

What is claimed is:

1. A process for preparing aldols by catalytic reaction of aldehydes and/or ketones, which comprises conducting said reaction in the channels of a microstructured reaction system.

2. The process of claim 1, wherein said channels have flow cross sections in the range from 50 $\mu m^2$ to 100 $mm^2$.

3. The process of claim 1, wherein a heterogeneous catalyst has been introduced into said microstructured reaction system.

4. The process of claim 1, wherein said catalyst is selected from the group consisting of basic anion exchanges, metal oxides of Mo, W, Ca, Mg and Al and basic zeolites.

5. The process of claim 1, wherein said reaction is conducted at pressures in the range from 1 to 50 bar absolute and at temperatures in the range from –10 to 250° C.

6. The process of claim 1, wherein an aldehyde RCHO is reacted with itself or with a second aldehyde $R_2$CHO or with a ketone $R_1R_2$CO or a ketone $R_1R_2$CO is reacted with itself or another ketone $R_3R_4$CO and $R_1$ to $R_4$, which are each identical or different, independently can have the following meanings:

$R_1$ is $C_1$–$C_{12}$-alkyl, $C_3$–$C_{12}$-cycloalkyl, aryl, or aralkyl having 14 or less carbon atoms, wherein said alkyl, said cycloalkyl, said aryl and said aralkyl each are substituted or unsubstituted;

$R_2$ is H, $C_1$–$C_{12}$-alkyl, $C_3$–$C_{12}$-cycloalkyl, aryl, or aralkyl having 14 or less carbon atoms, wherein said alkyl, said cycloalkyl, said aryl and said aralkyl each are substituted or unsubstituted;

$R_3$ is $C_1$–$C_{12}$-alkyl, $C_3$–$C_{12}$-cycloalkyl, aryl, or aralkyl having 14 or less carbon atoms, wherein said alkyl, said cycloalkyl, said aryl and said aralkyl each are substituted or unsubstituted;

$R_4$ is $C_1$–$C_{12}$-alkyl, $C_3$–$C_{12}$-cycloalkyl, aryl, or aralkyl having 14 or less carbon atoms, wherein said alkyl, said cycloalkyl, said aryl and said aralkyl each are substituted or unsubstituted.

7. The process of claim 6, wherein $R_1$ is an unsubstituted $C_1$–$C_{12}$-alkyl, an unsubstituted $C_3$–$C_{12}$-cycloalkyl, an unsubstituted aryl, or an unsubstituted aralkyl having 14 or less carbon atoms, $R_2$ is an unsubstituted $C_1$–$C_{12}$-alkyl, an unsubstituted $C_3$–$C_{12}$-cycloalkyl, an unsubstituted aryl, or an unsubstituted aralkyl having 14 or less carbon atoms, $R_3$ is an unsubstituted $C_1$–$C_{12}$-alkyl, an unsubstituted $C_3$–$C_{12}$-cycloalkyl, an unsubstituted aryl, or an unsubstituted aralkyl having 14 or less carbon atoms, $R_4$ is an unsubstituted $C_1$–$C_{12}$-alkyl, an unsubstituted $C_3$–$C_{12}$-cycloalkyl, an unsubstituted aryl, or an unsubstituted aralkyl having 14 or less carbon atoms.

8. The process of claim 1, wherein the residence time of said aldehydes or ketones or aldols in said channels is in the range from 0.001 to 1000 s.

9. The process of claim 1, wherein said reaction system is supplemented by a delay time zone which is not microstructured.

10. The process of claim 1, which further comprises the use of microreactor or micromixer.

11. The process of claim 10, wherein a heterogeneous catalyst has been introduced into said micromixer or said microreactor.

12. The process of claim 3, wherein said channels have flow cross sections in the range from 5,000 $\mu m^2$ to 5 $mm^2$.

13. The process of claim 12, wherein the reaction is carried out at temperatures in the range of 50 to 200° C.

14. The process of claim 13, wherein the residence time of said aldehydes or ketones or aldols and said channels is in the range from 0.01 to 100 seconds.

* * * * *

UNITED STATES PATENT AND TRADEMARK OFFICE
CERTIFICATE OF CORRECTION

PATENT NO.   : 6,437,190 B1
DATED        : August 20, 2002
INVENTOR(S)  : Leipprand et al.

It is certified that error appears in the above-identified patent and that said Letters Patent is hereby corrected as shown below:

Column 3,
Line 29, delete "RCHO" and insert -- $R_1CHO$ --.

Signed and Sealed this

Fourth Day of February, 2003

JAMES E. ROGAN
*Director of the United States Patent and Trademark Office*